US010456509B2

(12) United States Patent
Menon et al.

(10) Patent No.: US 10,456,509 B2
(45) Date of Patent: *Oct. 29, 2019

(54) CHLORHEXIDINE GLUCONATE COMPOSITIONS, RESIN SYSTEMS AND ARTICLES

(71) Applicant: 3M INNOVATIVE PROPERTIES COMPANY, Saint Paul, MN (US)

(72) Inventors: Vinod P. Menon, Woodbury, MN (US); Joseph D. Rule, Woodbury, MN (US); Richard B. Ross, Cottage Grove, MN (US); Deena M. Conrad-Vlasak, Midland, MI (US); Katie F. Wlaschin, Saint Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/262,981

(22) Filed: Jan. 31, 2019

(65) Prior Publication Data

US 2019/0160209 A1  May 30, 2019

Related U.S. Application Data

(63) Continuation of application No. 16/002,763, filed on Jun. 7, 2018, now Pat. No. 10,232,093, which is a continuation of application No. 15/627,548, filed on Jun. 20, 2017, now Pat. No. 10,016,537, which is a continuation of application No. 15/185,165, filed on Jun. 17, 2016, now Pat. No. 9,713,659, which is a continuation of application No. 14/424,186, filed as application No. PCT/US2013/056823 on Aug. 27, 2013, now abandoned.

(60) Provisional application No. 61/694,088, filed on Aug. 28, 2012.

(51) Int. Cl.
| | | |
|---|---|---|
| *A61L 31/16* | (2006.01) | |
| *A61L 15/44* | (2006.01) | |
| *A61L 15/46* | (2006.01) | |
| *A61L 15/58* | (2006.01) | |
| *A61L 31/14* | (2006.01) | |

(52) U.S. Cl.
CPC ............ *A61L 31/16* (2013.01); *A61L 15/44* (2013.01); *A61L 15/46* (2013.01); *A61L 15/58* (2013.01); *A61L 31/14* (2013.01); *A61L 2300/206* (2013.01); *A61L 2300/404* (2013.01)

(58) Field of Classification Search
None
See application file for complete search history.

(56) References Cited

U.S. PATENT DOCUMENTS

| | | |
|---|---|---|
| 4,310,509 A | 1/1982 | Berglund et al. |
| 4,340,043 A | 7/1982 | Seymour |
| 4,460,369 A | 7/1984 | Seymour |
| 4,533,669 A | 8/1985 | Yamanaka et al. |
| 4,643,180 A | 2/1987 | Feld et al. |
| 4,643,181 A | 2/1987 | Brown |
| 4,941,882 A | 7/1990 | Ward et al. |
| 5,017,617 A | 5/1991 | Kihara et al. |
| 5,017,625 A | 5/1991 | Ansell |
| 5,045,601 A | 9/1991 | Capelli et al. |
| 5,069,907 A | 12/1991 | Mixon et al. |
| 5,093,109 A | 3/1992 | Mausner |
| 5,098,711 A | 3/1992 | Hill et al. |
| 5,270,358 A | 12/1993 | Asmus |
| 5,357,636 A | 10/1994 | Dresdner, Jr. et al. |
| 5,369,155 A | 11/1994 | Asmus |
| 5,536,768 A | 7/1996 | Kantner et al. |
| 5,603,921 A | 2/1997 | Bowen |
| 5,614,310 A | 3/1997 | Delgado et al. |
| 5,660,178 A | 8/1997 | Kantner et al. |
| 5,717,005 A | 2/1998 | Richardson |
| 5,908,693 A | 6/1999 | Delgado et al. |
| 6,458,341 B1 | 10/2002 | Rozzi et al. |
| 6,592,912 B1 | 7/2003 | Barabolak et al. |
| 6,844,306 B2 | 1/2005 | Werle et al. |
| 7,005,031 B2 | 2/2006 | Lucast et al. |
| 9,713,659 B2 * | 7/2017 | Menon ............... A61L 31/16 |
| 10,016,537 B2 * | 7/2018 | Menon ............... A61L 31/16 |
| 2001/0026810 A1 | 10/2001 | McGhee et al. |
| 2002/0037945 A1 | 3/2002 | Nielsen |
| 2003/0007999 A1 | 1/2003 | Blatchford et al. |
| 2003/0031694 A1 | 2/2003 | Anderson |
| 2003/0175503 A1 | 9/2003 | Lucast et al. |
| 2004/0247655 A1 | 12/2004 | Asmus et al. |
| 2005/0245738 A1 | 11/2005 | Singh |
| 2005/0249791 A1 | 11/2005 | Hobbs et al. |
| 2005/0250871 A1 | 11/2005 | Bublewitz |
| 2005/0271611 A1 | 12/2005 | Yoshida |

(Continued)

FOREIGN PATENT DOCUMENTS

| | | |
|---|---|---|
| CA | 1098826 | 4/1981 |
| DE | 20204160 | 7/2002 |
| EP | 1 358 894 | 11/2003 |
| EP | 1 787 637 | 5/2007 |
| EP | 1 882 480 | 1/2008 |
| FR | 2 379 284 | 1/1978 |

(Continued)

OTHER PUBLICATIONS

Belmares, M. et al.; "Hildebrand and Hansen Solubility Parameters from Molecular Dynamics with Applications to Electronic Nose Polymer Sensors"; Journal of Computational Chemistry; vol. 25, No. 15; 2004; pp. 1814-1826.

(Continued)

*Primary Examiner* — Brian J Davis

(57) ABSTRACT

Compositions containing chlorhexidine gluconate solubilized in hydrophobic vehicles are described. Resin systems containing such chlorhexidine gluconate compositions, including adhesives and articles incorporating such resin systems, including medical articles such as drapes are also described.

20 Claims, 1 Drawing Sheet

(56) References Cited

U.S. PATENT DOCUMENTS

| | | |
|---|---|---|
| 2006/0051385 A1 | 3/2006 | Scholz |
| 2006/0205838 A1 | 9/2006 | Velamakanni |
| 2007/0036846 A1 | 2/2007 | Tsang |
| 2008/0057007 A1 | 3/2008 | Leonhardt et al. |
| 2008/0063695 A1 | 3/2008 | Vitaris |
| 2008/0064711 A1 | 3/2008 | Friedman |
| 2008/0142023 A1 | 6/2008 | Schmid et al. |
| 2010/0022654 A1 | 1/2010 | Asmus et al. |
| 2010/0158752 A1 | 6/2010 | Friderich et al. |
| 2010/0196504 A1 | 8/2010 | Schmaus et al. |

FOREIGN PATENT DOCUMENTS

| | | |
|---|---|---|
| GB | 1599159 | 9/1981 |
| JP | 53-101520 | 9/1978 |
| JP | H03-99010 | 4/1991 |
| JP | 2003-081801 | 3/2003 |
| JP | 2007-217394 | 8/2007 |
| JP | 2007-307287 | 11/2007 |
| WO | WO 1996/14094 | 5/1996 |
| WO | WO 2008/057773 | 5/2008 |
| WO | WO 2008/157092 | 12/2008 |
| WO | WO 2009/088894 | 7/2009 |
| WO | WO 2010/080936 | 7/2010 |
| WO | WO 2010/129199 | 11/2010 |
| WO | WO 2010/129227 | 11/2010 |
| WO | WO 2011/117384 | 9/2011 |
| WO | WO 2014/035971 | 3/2014 |

OTHER PUBLICATIONS

Denton, "Chlorhexidine" Chapt. 16, 3M CHG Preoperative Preparation Original IND Nov. 2006, pp. 724-739.

Disperse Definition, Cambridge Dictionary, retrieved online on Nov. 17, 2016, Nov. 17, 2016, http://dictionary.cambridge.org/dictionary/english/disperse.

Gadhave, "Determination of Hydrophilic-Lipophilic Balance Value," International Journal of Science and Research (IJSR), ISSN (Online): 2319-7064, Institute of Chemical Technology Maharashtra, India, vol. 3 Issue 4, Apr. 2014 www.ijsr.net.

Griffin, W.C.; "Calculation of HLB Values of Non-Ionic Surfactants"; Journal of the Society of Cosmetic Chemists; 1954; pp. 249-256.

Grove, G.L. et al.; "Comparison of Two Preoperative Skin Antiseptic Preparations and Resultant Surgical Incise Drape Adhesion to Skin in Healthy Volunteers"; The Journal of Bone and Joint Surgery; vol. 94A, No. 13; 2012; pp. 1187-1192.

Lin, Y. et al.; "Glycerol Monolaurate and Dodecylglycerol Effects on *Staphylococcus aureus* and Toxic Shock Syndrome Toxin-1 In Vitro and In Vivo"; PLoS ONE; vol. 4, No. 10; 2009; e7499; 10 pgs.

Mayo, S.L. et al.; "DREIDING: A Generic Force Field for Molecular Simulations"; J. Phys. Chem.; vol. 94; 1990; pp. 8897-8909.

Mierlo, "Comparison of Hydrophile-Lipophile Balance of Glycerol, DMGP, and DOP with the Activity Coefficient of Water at Infinite Dilution in the Compound," Notes, Journal of Colloid and Interface Science, vol. 127, No. 2, Feb. 1989, pp. 583-585.

Preuss, "Minimum inhibitory concentrations of herbal essential oils and monolaurin for gram-positive and gram-negative bacteria," Molecular and Cellular Biochemistry 272: 29-34, 2005, Springer 2005, pp. 29-34.

Rappe, A.K. et al.; "Charge Equillbration for Molecular Dynamics Simulations"; J. Phys. Chem.; vol. 95; 1991; pp. 3358-3363.

Vinod Menon Declaration under 37 C.F.R. §1.132, Feb. 9, 2017, (U.S. Appl. No. 14/424,198).

Zhang, H. et al.; "Molecular dynamics simulations on the interaction between polymers and hydroxyapatite with and without coupling agents"; Acta Biomaterialia; vol. 5; 2009; pp. 1169-1181.

Zhang et al., Antibacterial Interactions of Monolaurin with Commonly Used Antimicrobials and Food Components, Journal of Food Science—vol. 74, Nr. 7, 2009, p. 418-421.

* cited by examiner

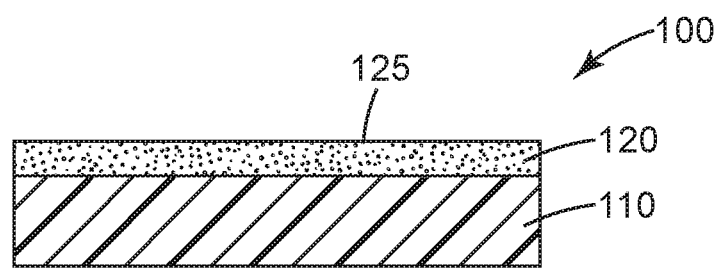

CHLORHEXIDINE GLUCONATE COMPOSITIONS, RESIN SYSTEMS AND ARTICLES

CROSS REFERENCE TO RELATED APPLICATIONS

This application is a continuation of U.S. application Ser. No. 16/002,763, filed Jun. 7, 2018; which is a continuation of U.S. application Ser. No. 15/627,548, filed Jun. 20, 2017, and issued as U.S. Pat. No. 10,016,537 on Jul. 10, 2018; which is a continuation of U.S. application Ser. No. 15/185, 165, filed Jun. 17, 2016, and issued as U.S. Pat. No. 9,713,659 on Jul. 25, 2017; which is continuation of U.S. application Ser. No. 14/424,186, filed Feb. 26, 2015, now abandoned; which is a national stage filing under 35 U.S.C. 371 of PCT/US2013/056823, filed Aug. 27, 2013; and which claims priority to U.S. Provisional Patent Application No. 61/694,088, filed Aug. 28, 2012, the disclosures of which are incorporated by reference in their entirety herein.

FIELD

The present disclosure relates to compositions containing chlorhexidine gluconate solubilized in hydrophobic vehicles, and resin systems containing such chlorhexidine gluconate compositions, including adhesives. The present disclosure also relates to articles incorporating such resin systems, including medical articles such as drapes.

SUMMARY

Briefly, in one aspect, the present disclosure provides a composition comprising chlorhexidine gluconate solubilized in a hydrophobic vehicle having a hydrophilic-lipophilic balance of no greater than 10 as determined using the HLB Method. In some embodiments, the hydrophobic vehicle comprises two proximate hydrogen-bonding groups, wherein at least one of the hydrogen-bonding groups is a hydrogen donor. In some embodiments, the hydrophobic vehicle comprises an ester group, e.g., a monoacylglycerol. In some embodiments, the hydrophobic vehicle comprises an ether group, e.g., dipropylene glycol and glyceryl monoalkyl ethers. In some embodiments, the hydrophobic vehicle comprises an alcohol having proximate hydroxyl groups, e.g., 1,2-octanediol, 1,2-decanediol, and combinations thereof.

In some embodiments, the composition comprises no greater than 1 part by weight hydrophilic vehicle per 1 part by weight chlorhexidine gluconate. In some embodiments, the composition comprises no greater than 0.1 parts by weight hydrophilic vehicle per 1 part by weight chlorhexidine gluconate. In some embodiments, the composition comprises no greater than 0.1 parts by weight water per 1 part by weight chlorhexidine gluconate.

In some embodiments, the composition further comprises a resin system comprising a polymer. In some embodiments, the resin system comprises a hydrophobic phase, wherein the hydrophobic vehicle plasticizes the hydrophobic phase. In some embodiments, the polymer comprises an acrylate polymer. In some embodiments, the polymer comprises a block copolymer polymer. In some embodiments, the resin system is a pressure sensitive adhesive.

In some embodiments, the composition comprises at least 0.2 wt. % CHG, based on the total weight of the composition. In some embodiments, the composition comprises at least 0.5 wt. % and no greater than 5.0 wt. % CHG, based on the total weight of the composition.

In another aspect, the present disclosure provides an article comprising a substrate and a composition according to the present disclosure bonded to at least a portion of a surface of the substrate. In some embodiments, the composition is a pressure sensitive adhesive. In some embodiments, the substrate is selected from the group consisting of films, nonwovens, wovens, and combinations thereof. In some embodiments, the substrate comprises at least one of polyalkylenes, polyesters, polyamides, and polyurethanes. In some embodiments, the article is a medical article, e.g., a drape or a dressing.

The above summary of the present disclosure is not intended to describe each embodiment of the present invention. The details of one or more embodiments of the invention are also set forth in the description below. Other features, objects, and advantages of the invention will be apparent from the description and from the claims.

BRIEF DESCRIPTION OF THE DRAWINGS

The FIGURE illustrates an exemplary article incorporating a composition according to some embodiments of the present disclosure.

DETAILED DESCRIPTION

Chlorhexidine digluconate, commonly referred to as "chlorhexidine gluconate" or "CHG," is an antimicrobial useful in various applications. CHG is often provided as an aqueous solution, in part because CHG may degrade in a non-aqueous composition. CHG has been provided in non-aqueous solutions by replacing water with a hydrophilic vehicle. Consistent with typical usage, as used herein, a "hydrophilic vehicle" is one having a hydrophile/lipophile balance ("HLB") of greater than 10. For example, U.S. Pat. No. 6,458,341 (Rozzi et al., issued Oct. 1, 2002) describes non-aqueous solutions containing CHG and a solubilizing glycol, which is an exemplary hydrophilic vehicle.

Surprisingly, the present inventors have discovered that CHG can be solubilized in a wide variety of hydrophobic vehicles. Consistent with typical usage, as used herein, a "hydrophobic vehicle" is one having a hydrophile/lipophile balance ("HLB") of no greater than 10. Examples of such hydrophobic vehicles include monoacylglycerides as described in International Publication No. WO2014/035971.

There are at least three distinct methods for preparing solutions of CHG in a non-aqueous vehicle. The first method involves mixing an aqueous CHG solution with a relatively high boiling vehicle, and then pulling a vacuum on the mixture to remove the water (the "Vacuum Method"). The second method involves lyophilizing CHG, and then dissolving the CHG into the vehicle (the "Lyophilizing Method"). The third method involves generating the CHG in situ by reacting gluconolactone, a limited amount of water, and chlorhexidine free base (the "In Situ Method). Each method appears to give a similar final product, but each method has advantages and disadvantages. For example, the lyophilization route does not require exposing the CHG to sustained heat, which helps prevent degradation. The liquid vacuum stripping route is easily scalable using readily available manufacturing equipment, e.g., kettles. The in situ generation method does not require vacuum-equipped reactors.

All the methods may leave small amounts of water behind. Therefore, as used herein, "non-aqueous" refers to compositions that may contain small amounts of water, e.g., less than 1 wt. %. In some embodiments, the compositions contain less than 0.5 wt. %, e.g., less than 0.1 wt. % or even less than 0.01 wt. % water. In some embodiments, the compositions comprise no greater than 1 part by weight water per 1 part by weight CHG, no greater than 0.5 part by weight, no greater than 0.1 part by weight, or even no greater than 0.01 part by weight water per 1 part by weight CHG.

In some embodiments, the compositions contain little or no hydrophilic vehicle. As used herein, water is considered a separate component independent of any hydrophilic vehicles; therefore, the following amounts are exclusive of any water which may be present in the composition. In some embodiments, the compositions comprise no greater than 2 parts by weight hydrophilic vehicle per 1 part by weight CHG, e.g., no greater than 1 part by weight, no greater than 0.5 part by weight, or even no greater than 0.1 part by weight hydrophilic vehicle per 1 part by weight CHG.

In the present disclosure, HLB values are calculated using the method of Griffin (Griffin W C; J. Soc. of Cosmetic Chemists, pp. 249-256 (1954)). Thus, as used herein, the "HLB Method" involves a calculation based on the following:

$$HLB = (E+P)/5,$$

where E is the weight percent of oxyethylene content and P is the weight percent of polyhydric alcohol content (glycerol, sorbitol, etc.). For the compounds herein, glycerol segments with two hydroxyl groups, glycerol segments with one hydroxyl group, and hydroxyl-containing segments of any additional polyhydric molecules were included in the definition of P.

As used in the present disclosure, hydrophilic vehicles have an HLB value as calculated using the HLB Method of greater than 10. In some embodiments, the hydrophilic vehicle has an HLB value of greater than 11, e.g., greater than 12. Hydrophobic vehicles have an HLB value as calculated using the HLB Method of no greater than 10. In some embodiments, the hydrophobic vehicle has an HLB value of no greater than 9, e.g., no greater than 7.

Other methods of calculating HLB are available and may be required when determining the HLB value for compounds lacking both E and P groups, as defined above. While the calculated value of HLB may vary depending on the method used, the trends and relative hydrophobicity of materials are expected to be similar.

In some embodiments, hydrophobic vehicles having proximate hydroxyl groups, e.g., vicinal hydroxyl groups, may be useful. As used herein, "proximate" groups refer to groups separated by no more than three carbon atoms, as illustrated in Formulas I (hydroxyl groups separated by two carbon atoms) and II (hydroxyl groups separated by three carbon atoms). In some embodiments, the proximate groups may be vicinal, i.e., separated by two carbon atoms, as illustrated in Formula I.

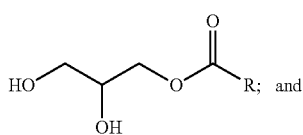

(I)

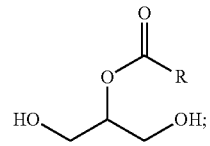

(II)

wherein RC=O is the acyl group. The depiction of 1-monoacylglycerides (Formula I) and 2-monoacylglycerides (Formula II) is merely intended to illustrate the meaning of proximate and vicinal groups and is not intended to, and does no limit the present invention to such monoacylglycerides.

In some embodiments, the compositions comprise at least 5% by weight CHG dissolved in the non-aqueous vehicle based on the combined weight of the CHG and the vehicle. In some embodiments, the compositions comprise at least 10%, at least 15%, or even at least 20% by weight CHG dissolved in the non-aqueous vehicle.

In some embodiments, compositions of the present disclosure comprising CHG solubilized in a hydrophobic vehicle may be applied directly to a substrate, e.g., sprayed or otherwise coated onto a porous or non-porous substrate. However, in addition to discovering that CHG could be solubilized in hydrophobic vehicles, the present inventors also discovered that, when solubilized in a hydrophobic vehicle, CHG could be incorporated into a resin system such that the CHG remains available and effective as an antimicrobial agent.

Depending on the hydrophobic vehicle, CHG may be incorporated into a wide variety of resin systems. In some embodiments, one or more components of the resin systems are themselves hydrophobic, and are thus compatible with the hydrophobic vehicle. In some embodiments, the resin system may include both hydrophilic and hydrophobic components and/or phases, wherein the hydrophobic vehicle is compatible with at least the hydrophobic portion. In some embodiments, the hydrophobic vehicle is selected such that it plasticizes (i.e., is compatible with and lowers the glass transition temperature of) the hydrophobic component or phase. In some embodiments, the hydrophobic vehicle is able to migrate through the resin system, carrying the solubilized CHG. For example, in some embodiments, the hydrophobic vehicle and solubilized CHG are able to migrate to a surface of a layer of the resin system providing a replenishable supply of CHG to such a surface.

Generally, the resin system includes at least one polymer. In some embodiments, the resin system includes at least one hydrophobic polymer or phase. Suitable polymers include polyesters, polyester polyols, polyurethanes, polyalkylenes, acrylates, rubbers, block copolymers, and combinations thereof. In some applications, the resin system may be an adhesive, e.g., a pressure sensitive adhesive ("PSA").

In some embodiments, the PSA comprises an acrylic polymer or copolymer comprising the reaction product of a mixture comprising at least one alkyl (meth)acrylate monomer. As used herein, "(meth)acrylate" refers to an acrylate and/or methacrylate. For example, butyl (meth)acrylate refers to butyl acrylate and/or butyl methacrylate. In some embodiments, the mixture may also include a crosslinking agent.

In some embodiments, the alkyl group of at least one alkyl (meth)acrylate contains 4 to 18 carbon atoms. In some embodiments, this alkyl group contains at least 5 carbon atoms. In some embodiments, this alkyl group contains no greater than 8 carbon atoms. In some embodiments, the alkyl group of the first alkyl (meth)acrylate has eight carbon atoms, e.g., isooctyl (meth)acrylate and/or 2-ethylhexyl (meth)acrylate.

In some embodiments, the mixture may comprise one or more additional monomers including one or more additional alkyl(meth)acrylates. In some embodiments, the alkyl group of at least one of the additional alkyl (meth)acrylates contains no greater than 4 carbon atoms. In some embodiments, the alkyl group of at least one alkyl (meth)acrylate has 4 carbon atoms, e.g., butyl (meth)acrylate. In some embodiments, the alkyl group of at least one alkyl (meth)acrylate has 1-2 carbon atoms, e.g., methyl acrylate and/or ethyl acrylate.

Examples of suitable polar monomers that may be copolymerized with the alkyl (meth)acrylate monomers include acidic monomers such as carboxylic acid monomers as well as various acrylamides. Particular examples of polar monomers include vinyl carboxylic acids such as acrylic acid, methacrylic acid, itaconic acid, maleic acid, fumaric acid, and 2-hydroxyethyl acrylate or methacrylate. Other suitable polar monomers include N-vinyl pyrrolidone, N-vinyl caprolactam, acrylamide, methacrylamide, N-substituted and N,N-disubstituted acrylamides such as N-ethyl acrylamide, N-hydroxyethyl acrylamide, N,N-dimethyl acrylamide, N,N-diethyl acrylamide, and N-ethyl, N-dihydroxyethyl acrylamide, acrylonitrile, methacrylonitrile and maleic anhydride. Various combinations of such polar monomers can be employed.

Optionally, one or more monoethylenically unsaturated co-monomers may be polymerized with the acrylate or methacrylate monomers. One group of useful co-monomers includes those having a homopolymer glass transition temperature greater than the glass transition temperature of the (meth)acrylate homopolymer. Examples of suitable co-monomers falling within this group include acrylic acid, acrylamides, methacrylamides, substituted acrylamides (such as N,N-dimethyl acrylamide), itaconic acid, methacrylic acid, acrylonitrile, methacrylonitrile, vinyl acetate, N-vinyl pyrrolidone, isobornyl acrylate, cyano ethyl acrylate, N-vinylcaprolactam, maleic anhydride, hydroxyalkyl (meth)-acrylates, N,N-dimethyl aminoethyl (meth)acrylate, N,N-diethylacrylamide, beta-carboxyethyl acrylate, vinyl esters of neodecanoic, neononanoic, neopentanoic, 2-ethylhexanoic, or propionic acids (e.g., those available from Union Carbide Corp. of Danbury, Conn., under the designation VYNATES), vinylidene chloride, styrene, vinyl toluene, and alkyl vinyl ethers.

A second group of monoethylenically unsaturated co-monomers that may be polymerized with the acrylate or methacrylate monomers includes those having a homopolymer glass transition temperature (Tg) less than the glass transition temperature of the (meth)acrylate homopolymer. Examples of suitable co-monomers falling within this class include ethoxyethoxyethyl acrylate (Tg=−71 degrees Celsius) and a methoxypolyethylene glycol 400 acrylate (Tg=−65 degrees Celsius; available from Shin Nakamura Chemical Co., Ltd. Japan, under the designation "NK Ester AM-90G").

In some embodiments, the PSA comprises a block copolymer. In some embodiments, the block copolymer is a styrenic block copolymer, i.e., a block copolymer comprising at least one styrene hard segment, and at least one elastomeric soft segment. Exemplary styrenic block copolymers include dimmers such as styrene-butadiene (SB) and styrene-isoprene (SI). Additional exemplary styrenic block copolymers include styrene-isoprene-styrene (SIS), styrene-butadiene-styrene (SBS), styrene-ethylene/butadiene-styrene (SEBS), and styrene-ethylene/propylene-styrene block copolymers. In some embodiments, radial and star block copolymers may be used. Commercially available styrenic block copolymers include those available under the trade designation KRATON from Kraton Polymers LLC. including, e.g., KRATON D SBS and SIS block copolymers; and KRATON G SEBS and SEPS copolymers. Additional commercially available di- and tri-block styrenic block copolymers include those available under the trade designations SEPTON and HYBAR from Kuraray Co. Ltd., those available under the trade designation FINAPRENE from Total Petrochemicals, and those available under the trade designation VECTOR from Dexco Polymers LP.

The resin systems of the present disclosure may contain any of a variety of known additives including, e.g., crosslinkers, photoinitiators, curing agents, tackifiers, plasticizers, fillers, dyes, pigments, and the like. As used herein, the terms tackifier and plasticizer are used relative to the material or phase into which they are incorporated. Thus, a "tackifier" is a material that is compatible with and raises the glass transition temperature of a material; while a "plasticizer" is a material that is compatible with and lowers the glass transition temperature of a material.

Examples

Objects and advantages of various embodiments of the present disclosure are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight.

Solubility Screening. Screening tests were conducted to determine the solubility of CHG in a wide variety of vehicles. Tests were conducted using the Vacuum Method and the Lyophilizing Method.

Vacuum Method. A 25 g sample of a CHG/water solution (20 wt. % solution in water, obtained from Xttrium Laboratories Inc., Chicago, Ill.) was added to 45 g of the vehicle of interest in a 200 mL round bottom flask. The flask was put in a 60° C. oil bath and stirred with a magnetic stir bar. Vacuum (less than 3.3 kilopascal (25 Torr)) was pulled until bubbling stopped and the weight had closely approached the theoretical value of 50 grams—usually 30-90 minutes. In some cases, the vehicle was somewhat volatile and the weight of the solution decreased significantly below 50 grams. In those cases, after nearly all the water was removed, additional vehicle was added to bring the final weight to 50 grams. The resulting concentration of CHG and residual water were determined. Also, the final state of the solution was qualitatively evaluated to determine if the mixture was transparent and apparently homogenous, or clearly inhomogeneous.

The results obtained using simple alcohols (i.e., compounds with only hydroxyl groups, carbon-carbon bonds, and carbon-hydrogen bonds) are summarized in Tables 1a and 1b. The results obtained using compounds with ester groups are summarized in Tables 2a and 2b. The results obtained using compounds with ether groups are summarized in Tables 3a and 3b.

TABLE 1a

Simple alcohols as non-aqueous vehicles providing good CHG solubility.

| Compound | CHG wt. % | Water wt. % | Temperature | Final State |
|---|---|---|---|---|
| Glycerol | 10% | 0.7% | 23-50° C. | Homogeneous |
| 1,2-propanediol | 10% | 3.1% | 23-50° C. | Homogeneous |
| 1,2-pentanediol | 50% | 3.3% | 23-50° C. | Homogeneous |
| 1,2-octanediol | 10% | 0.2% | 23-50° C. | Homogeneous |
|  | 20% | 0.3% | 23-50° C. | Homogeneous |
| 1,2,6-trihydroxyhexane | 10% | 0.5% | 23-50° C. | Homogeneous |
| 1,3-propanediol | 10% | 0.7% | 23-50° C. | Homogeneous |
| 1,4-butanediol | 10% | 1.7% | 23-50° C. | Homogeneous |
| 2-butene-1,4-diol | 10% | 1.2% | 23-50° C. | Homogeneous |
| 1,3-butanediol | 10% | 2.2% | 23° C. | Inhomogeneous |
|  |  |  | 50° C. | Homogeneous |
|  | 5% | 2.1% | 23-50° C. | Homogeneous |
| 3-methyl-1,3-butanediol | 10% | N.T. | 23-50° C. | Inhomogeneous |
|  | 5% | N.T. | 23-50° C. | Inhomogeneous |
|  | 2.5% | 1.1% | 23° C. | Inhomogeneous |
|  |  |  | 50° C. | Homogeneous |
|  | 1% | 1.2% | 23° C. | Inhomogeneous |
|  |  |  | 50° C. | Homogeneous |
| 1,3-cyclohexanediol | 10% | 1.6% | 23° C. | Inhomogeneous |
|  |  |  | 50° C. | Homogeneous |
|  | 6% | 4.8% | 23° C. | Inhomogeneous |
|  |  |  | 50° C. | Homogeneous |
| 2,3-butanediol | 10% | 1.2% | 23-50° C. | Homogeneous |
| 50% 1,2-hexanediol 50% 1,2-pentanediol | 20% | N.T. | 23-50° C. | Homogeneous |

TABLE 1b

Simple alcohols as non-aqueous vehicles providing poor CHG solubility.

| Compound | CHG wt. % | Temperature | Final State |
|---|---|---|---|
| 1,5-pentanediol | 10% | 23-50° C. | Inhomogeneous |
| 1,8-octanediol | 10% | 23-50° C. | Inhomogeneous |
| 2,5-hexanediol | 10% | 23-50° C. | Inhomogeneous |
| 2,3-dimethyl-2,3-butanediol | 10% | 23-50° C. | Inhomogeneous |
| 1,4-cyclohexanediol | 10% | 23-50° C. | Inhomogeneous |
| 1-octanol | 10% | 23-50° C. | Inhomogeneous |

Several trends were identified from the data in Tables 1a and 1b. 1,2-diols appear to impart CHG solubility. Other vicinal diols do not always impart solubility, particularly when sterically hindered (e.g. 2,3-dimethyl-2,3-butanediol). 1,3 diols appear to provide some solubility, but may require elevated temperature. 1,4-butanediol, which has two primary alcohol groups, provides solubility. Other diols similarly separated by four carbon atoms but with secondary alcohol groups do not provide good solubility (e.g., 2,5-hexanediol and 1,4-cyclohexanediol). Even through 1,5-pentanediol and 1,8-octanediol have two primary alcohol groups, the alcohol groups appear to be too widely separated to impart good solubility.

TABLE 2a

Vehicles with ester groups providing good CHG solubility.

| Compound | CHG. wt. % | Water wt. % | Temperature | Final State |
|---|---|---|---|---|
| Medium Chain Monoglyceride | 20% | 0.3% | 23-50° C. | Homogeneous |
| Glyceryl monostearate | 10% | 0.2% | 80° C. | Homogeneous |
| Glyceryl monocaprylate | 20% | ND | 60° C. | Homogeneous |
| Glyceryl monolaurate | 20% | 0.7% | 75° C. | Homogeneous |
| Glyceryl monoisostearate | 20% | ND | 60° C. | Homogeneous |
|  | 16% | 0.1% | 23-60° C. | Homogeneous |
|  | 10% | 0.7% | 23-60° C. | Homogeneous |
| Diethyl-D-Tartrate | 10% | 0.5% | 23-50° C. | Homogeneous |
| Diethyl-L-Tartrate | 10% | 0.3% | 23-50° C. | Homogeneous |
| Dibutyl-L-Tartrate | 10% | 0.1% | 23-50° C. | Homogeneous |
| Decaglyceryl tristearate | 10% | 1.7% | 23-50° C. | Homogeneous |
| Glyceryl monooleate | 20% | ND | 23-50° C. | Homogeneous |

ND = not determined

TABLE 2b

Vehicles with ester groups providing poor CHG solubility.

| Compound | CHG wt. % | Temperature | Final State |
|---|---|---|---|
| Dialkyl (C12 & C13) Tartrate | 10% | 23-50° C. | Inhomogeneous |
| Diisopropyl-L-Tartrate | 10% | 23-50° C. | Inhomogeneous |
| Diisopropyl-D-Tartrate | 10% | 23-50° C. | Inhomogeneous |
| Decaglyceryl pentaoleate | 10% | 23-50° C. | Inhomogeneous |
| Triglyceryl diisostearate | 10% | 23-50° C. | Inhomogeneous |
| PPG-5 Ceteth-20 | 10% | 23-50° C. | Inhomogeneous |
| Isolaureth-10 | 10% | 23-50° C. | Inhomogeneous |
| Polyglycerol-2-Triisostearate | 10% | 23-50° C. | Inhomogeneous |
| Dimer Diol | 5% | 23-50° C. | Inhomogeneous |
| Oxalic Acid Diethyl Ester | 10% | 23-50° C. | Inhomogeneous |

The trends observed for the esters in Tables 2a and 2b were similar to the trends identified for the simple alcohols. Monoglycerides tend to have a significant content of 1,2-diols and generally produce homogeneous solutions. Tartrates also have vicinal diols, but they do not have terminal hydroxyl groups. Tartrates with short alkyl chains produced homogeneous solutions, but when the alkyl groups become more bulky, the tartrates no longer produced homogeneity. With fatty acid esters of glycerol oligomers, it appears that the number of hydroxyl groups needs to be large compared to the number of non-polar fatty acid groups to achieve homogeneity.

TABLE 3a

Vehicles with ether groups providing good CHG solubility.

| Compound | CHG. wt. % | Water wt. % | Temperature | Final State |
|---|---|---|---|---|
| Triethylene glycol | 10% | 0.2% | 23-50° C. | Homogeneous |
| Tetraethylene glycol | 10% | 0.1% | 23-50° C. | Homogeneous |
| Triethyleneglycol monomethyl ether | 10% | 2.4% | 23-50° C. | Homogeneous |
| Diethyleneglycol monomethyl ether | 10% | 2.2% | 23-50° C. | Homogeneous |
| Diethyleneglycol monoethyl ether | 10% | ND | 23-50° C. | Inhomogeneous |
|  | 5% | ND | 23-50° C. | Inhomogeneous |
|  | 2.5% | 1.4% | 23-50° C. | Homogeneous |
| Dipropylene glycol | 10% | 0.5% | 23° C. | Inhomogeneous |
|  |  |  | 50° C. | Homogeneous |
|  | 5% | 1.5% | 23-50° C. | Homogeneous |
| Sorbeth-6 | 10% | ND | 23-50° C. | Homogeneous |
| 1,3-dihydroxyacetone dimer | 10% | 2.1% | 23-50° C. | Homogeneous |

TABLE 3a-continued

Vehicles with ether groups providing good CHG solubility.

| Compound | CHG. wt. % | Water wt. % | Temperature | Final State |
|---|---|---|---|---|
| Ethylhexyl glycerin | 10% | 0.1% | 23-50° C. | Homogeneous |
|  | 20% | 1.0% | 23-50° C. | Homogeneous |

TABLE 3b

Vehicles with ether groups providing poor CHG solubility.

| Compound | CHG wt. % | Temperature | Final State |
|---|---|---|---|
| Diethyleneglycol Monobutyl Ether | 10% | 23-50° C. | Inhomogeneous |
| Polyethyleneglycol Dimethyl Ether | 10% | 23-50° C. | Inhomogeneous |
| Diethyleneglycol Dimethyl Ether | 10% | 23-50° C. | Inhomogeneous |
| Tripropylene glycol | 10% | 23-50° C. | Inhomogeneous |
| Decaglyceryl pentaoleate | 10% | 23-50° C. | Inhomogeneous |
| Triglyceryl diisostearate | 10% | 23-50° C. | Inhomogeneous |
| PPG-5 Ceteth-20 | 10% | 23-50° C. | Inhomogeneous |

The trends observed with the ethers are somewhat different than those observed for the simple alcohols and ester-containing vehicles. Oligoethylene glycols with hydroxyl groups at each end of the chain tended to give homogenous solutions. As one of the hydroxyl groups is replaced with an ether the appearance of homogeneity seems to depend on the size of that ether group. On the other hand, propylene glycol oligomers are much less likely to give homogeneous solutions, and even the most favorable case—dipropylene glycol—only produced homogeneity at elevated temperatures or relatively low concentrations.

Based on the foregoing, the present inventors discovered that CHG can be solubilized in a wide variety of hydrophobic vehicles, as summarized in Table 4. HLB values calculated according to the HLB Method are included. Relying on these test methods and the trends observed in the results, one of ordinary skill in the art could readily identify additional such hydrophobic vehicles.

TABLE 4

Summary of hydrophobic vehicles providing good solubility for CHG.

| Class | Vehicle | HLB |
|---|---|---|
| alcohol | 1,2-octanediol | 8.4 |
| ester | Decaglyceryl tristearate | 9.7 |
| ester | Glyceryl monocaprylate | 8.4 |
| ester | Glyceryl monolaurate | 6.6 |
| ester | Glyceryl monostearate | 5.1 |
| ester | Glyceryl monoisostearate | 5.1 |
| ester | Glyceryl monooleate | 5.1 |
| ether | Dipropylene glycol | 9.1 |
| ether | Ethylhexyl glycerin | 8.9 |

The Lyophilization Method. Lyophilized CHG was prepared by freeze-drying the aqueous CHG solution (20 wt. % solution in water, obtained from Xttrium Laboratories Inc., Chicago, Ill.).

For lower viscosity vehicles, a 5 ml sample of the non-aqueous vehicle of interest was measured into a glass vial. For higher viscosity vehicles that were difficult to transfer by volume, a 5 gm sample was weighed into the vial. Next, 0.01 g of lyophilized CHG was added to the vial. The sample was capped and mixed by shaking for 30 seconds. The sample was immediately observed and then observed again after 2 minutes and again after 24 hours. After 24 hours, the sample was placed in a 50° C. oven for 2 hours and then removed and immediately observed. These samples were allowed to cool to room temperature and a final observation was made. The results are summarized in Table 5.

TABLE 5

Vehicles evaluated using 0.2 wt. % lyophilized CHG obtained by freeze-drying.

| Vehicle | Apparent solubility | | | | |
|---|---|---|---|---|---|
|  | immediate | 2 minutes | >24 hours | 2 hours 50° C. | after cooling |
| Acetyltriethyl citrate | no | no | partial | soluble | partial |
| Diisostearyl dimerate | no | no | no | soluble | no |
| Dipropylene glycol | no | no | soluble | soluble | soluble |
| Glycerol triisostearate | no | no | partial | partial | partial |
| Isostearate caprylic/capric glycerides | partial | partial | soluble | soluble | soluble |
| Glycereth-18 Ethylhexanoate | no | no | soluble | soluble | soluble |
| Isolaureth-10 | no | no | partial | soluble | soluble |
| PPG-5-ceteth-20 | no | no | partial | soluble | soluble |
| Octyldodeceth-10 | no | partial | partial | partial | partial |
| Oleth-2 | no | no | no | partial | partial |
| Isostearyl isostearate | no | no | no | partial | partial |
| PEG-20 glyceryl Triisostearate | no | partial | partial | partial | partial |
| Pentaerythritol tetraisostearate | partial | partial | partial | partial | partial |
| Polyglycerol-3 Diisostearate | no | no | soluble | soluble | partial |
| Propylene glycol Dicaprylate/caprate | no | no | partial | partial | partial |

Generally, the results were similar to those observed using the Vacuum Method. Specifically, polar functional groups, particular when close together, tended to provide CHG solubility. For some vehicles, CHG was soluble at the low concentrations used with the Lyophilization Method, but at least partially insoluble at the higher concentrations used in the Vacuum Method.

Generally, CHG is added to a composition such that its final concentration is at least 0.2 wt. %, in some embodiments at least 0.5 wt. %, in some embodiments at least 1.0 wt. %, in other embodiments at least 2.0 wt. %, in yet other implementations at least 5.0 wt. %, and in some cases exceeding 10 wt. %, based on the total weight of the composition. Generally, the CHG concentration is no greater than 25 wt. %, more preferably no greater than 20 wt. %, and most preferably no greater than 15 wt. %, based on the total weight of the composition. A typical range for CHG concentration to enhance active kill is at least 0.5 wt. % and no greater than 5.0 wt. %, based on the total weight of the composition.

As illustrated in the following examples, compositions comprising CHG solubilized in such vehicles can be incorporated into a wide variety of resin systems and in the preparation of a wide variety of articles. Materials used in the preparation of the examples are summarized in Table 6a and 6b.

TABLE 6a

Summary of materials used in the preparation of the examples.

| Name | Description | Trade Name and Source |
|---|---|---|
| CHG | chlorhexidine gluconate, 20 wt. % solution in water | Xttrium Laboratories, Inc., Chicago, Illinois |
| MRSA | Methicillin Resistant *Staphylococcus Aureus* | American Type Culture Collection (ATCC #33592), Manassas, Virginia |
| Film-1 | polyester elastomer film (HYTREL 4056 resin) | E. I. du Pont de Nemours & Co., Wilmington, Delaware |
| Resin systems | | |
| Res-1 | amorphous polyester polyol | PRIPLAST 3193, Croda Inc., Edison, NJ |
| Res-2 | amorphous polyester polyol | PRIPLAST 3197; Croda Inc. |
| Res-3 | amorphous polyester polyol | PRIPLAST 1838 (MW 2000); Croda Inc. |
| Res-4 | amorphous polyester polyol | PRIPLAST 3196 (MW 3000); Croda Inc. |
| PSA-1 | isooctyl acrylate/N-vinyl-pyrrolidone | 3M Company, St. Paul, Minnesota |
| PSA-2 | isooctyl acrylate/acrylamide | 3M Company |
| PSA-3 | isooctyl acrylate/vinyl acetate/acrylamide | 3M Company |
| PSA-4 | tackified KRATON block copolymer adhesive | 3M Company |

TABLE 6b

Summary of vehicles used in the preparation of the examples.

| HLB | Description | Trade Name and Source |
|---|---|---|
| Hydrophobic Vehicles | | |
| 8.9 | ethylhexyl glycerin | SENSIVA SC 50 Schulke & Mayr, Norderstedt, Germany |
| 8.4 | glycerol monocaprylate | Abitec Corp, Janesville, Wisconsin |
| 7.5 | sorbitan isostearate | Croda Inc. |
| 7.2 | decaglycerol pentaoleate | Barnet Products Corp, Englewood Cliffs, New Jersey |
| 7.0 | 1,2-decanediol | Symrise, Teterboro, NJ |
| 6.8* | medium chain monoglyceride (MCM-1) | MCM, Abitec Corp, Janesville, Wisconsin |
| 6.8 | medium chain monoglyceride (MCM-2) | MCM-NF, Abitec Corp. |
| 5.1 | glycerol monoisostearate (GMIS-1) | JEEN GMIS, Jeen Corp., Fairfield, NJ |
| 5.1 | glycerol monoisostearate (GMIS-2) | CRODA GMIS Croda Iberica, Barcelona, Spain |
| 5.1 | glycerol monoisostearate (GMIS-3) | LUBRIZOL GMIS Lubrizol Adv. Mtls., Cleveland, Ohio |
| 5.1 | glycerol monooleate | Gattefosse SAS, St. Priest, France |
| 3.3 | sorbitan trioleate | Aldrich Chemicals, Milwaukee, WI |
| Hydrophilic Vehicles | | |
| 11.7 | 1,2-pentanediol | Symrise, Teterboro, NJ |
| 15.9** | 1,2,3-triacetoxypropane (triacetin) | Aldrich Chemicals, Milwaukee, WI |
| 16.0 | 1,2-propanediol | Aldrich Chemicals, Milwaukee, WI |
| 20.0 | glycerol | EM Science, Gibbstown, New jersey |

*Estimate based on available compositional information
**Estimate based on literature values and modified calculations including C=O and glycerol groups as hydrophilic components.

CHG solutions. The solutions containing CHG were either a 20 wt. % aqueous solution of CHG or a 10-20% w/w solution of CHG in a non-aqueous vehicle. The non-aqueous solutions were prepared by freeze drying the aqueous CHG solution to produce lyophilized CHG. Finely divided, lyophilized CHG was then solubilized in a non-aqueous vehicle at room temperature with continuous stirring for eight hours.

Adhesive Preparation Procedure. Adhesive compositions were prepared by blending together a solvent-based pressure sensitive adhesive and a solution of CHG in a non-aqueous vehicle through simple manual agitation.

Adhesive Coating Procedure. Adhesive compositions were coated as hand-spreads by applying a uniform layer of the adhesive on the release surface of a suitable release liner using a knife-edge coater. The wet adhesive thickness ranged from 50 to 510 microns (2-20 mils). The coated adhesives were dried in a solvent oven for 1-10 minutes at temperatures between 65 and 93° C. (150 and 200° F.).

Adhesive Lamination Procedure. The dried adhesives were used to prepare adhesive articles samples by laminating the dried adhesive to a suitable backing using nip rollers at room temperature.

CHG Surface Availability Analysis. In some embodiments, a discrete amount of CHG should be available at the surface of the adhesive. Surface availability was determined by exposing the surface of the dried adhesive to water in a resting state, according to the following method. A sample of an adhesive article sufficient to cover a circular area of 660 square millimeters was cut from a larger section of an adhesive article prepared as described above. Water (4.0 mL) was pipetted into a glass cup. The release liner was removed exposing a surface of the dried adhesive, and the sample was applied evenly to the top of the glass cup and pressed tight to seal the adhesive to the glass cup so it did not leak when inverted. The sample was then inverted. After the desired test time had elapsed, the sample was reverted and immediately opened. An aliquot of the water was transferred to an LC vial for analysis. Samples were analyzed by reversed-phase HPLC using absorbance detection on an Agilent 1200 HPLC system consisting of a quaternary gradient pump, autosampler, heated column compartment and variable wavelength detector. 5.0 mcL portions of sample solutions were injected onto a MACMOD Analytical Inc. 150×3 mm ACE 3 micrometer C18 column. The column was equilibrated with 80/20 v/v water/methanol containing 40 mM pH 3.7 ammonium formate buffer at 0.50 mL/min and 40° C. Following injection the samples were eluted with a 30 min linear gradient to 20/80 v/v water/methanol containing 40 mM pH 3.7 ammonium formate buffer. This eluent composition was held isocratically for 5 minutes before re-equilibration in the starting eluent. Absorbance detection of the 254±2 nm signal was utilized to quantify sample concentration of chlorhexidine gluconate against standard solutions containing chlorhexidine acetate ("CHA"). A molar fraction of 1.435 was applied to the quantitation to account for the molar ratio of CHG/CHA (898/626).

Direct Time Kill Analysis. Specimens of several coated adhesives were subjected to antimicrobial performance testing according to the following 5-30 minute time kill study. A suspension of methicillin resistant *Staphylococcus aureus* (MRSA, ATCC #33592) was prepared at a concentration of 1×10$^8$ CFU (colony forming units) per milliliter (mL) in phosphate buffered water (pbw) using a 0.5 McFarland Equivalence Turbidity Standard. Using an Eppendorf pipette, 50 micro liters (μL) of this suspension was transferred as 15-16 separate droplets to the adhesive surface of a 2.5 cm diameter section of an adhesive film. These inoculated specimens were then incubated at room temperature (23+/−2° C.) for 5-30 minutes. After incubation, the specimens were placed in 20 mL of neutralizing buffer and sonicated for one minute followed by vortexing for two minutes. Portions of the resulting solution were serially diluted with pbw. The neat solution and dilutions were each plated to 3M PETRIFILM aerobic count plates (3M Company) and incubated for at least 24 hours. The 3M PETRIFILM plates were then counted using a 3M PETRIFILM plate reader (model 6499, 3M Company).

Example Set A. These examples show the antimicrobial efficacy of several CHG containing resin systems using the Direct Time Kill Analysis. Generally, the CHG was solubilized in a hydrophobic vehicle. The hydrophobic vehicle was compatible with and plasticized (i.e., reduced the Tg of) the hydrophobic phase of the base adhesive. The formulations were prepared by premixing the hydrophobic vehicle(s) with aqueous CHG, diluting with heptane, and mixing the solution with the solvent-based adhesive. The resulting mixture was coated on a silicone release liner at 4.6 mg/square centimeter, dried and laminated to Film-1. When the water phase evaporated from the adhesive, it left behind CHG solubilized in the hydrophobic vehicle, which was dispersed in the adhesive. The adhesives were tested for antimicrobial activity using the Direct Time Kill Analysis with an incubation period of 5 minutes. The formulations and log reduction results are shown in Table 7. All the examples containing CHG solubilized in a vehicle that plasticized the adhesive showed good bactericidal activity at five minutes relative to the sample without CHG, i.e., Comparative Example (CE-1).

Example Set B. These examples showed the effect of using hydrophilic non-aqueous vehicles that did not plasticize the adhesive as compared to the hydrophobic non-aqueous vehicles that did plasticize the adhesive. The formulations were prepared by premixing the vehicle or vehicle blends with aqueous CHG, diluting with heptane, and mixing the solution with a solvent-based adhesive. All samples contained 2 wt. % CHG and used PSA-2 except Comparative Example CE-2, which used PSA-1. The resulting mixture was coated on a silicone release liner at 4.6 mg/square centimeter, dried and laminated to Film-1. The adhesives were tested for antimicrobial activity according to the Direct Kill Time Analysis, with an incubation period of 5 minutes. The compositions and log reduction results are shown in Table 8.

TABLE 8

Compositions (wt. %) and log reductions for samples containing 2 wt. % CHG.

| EX. | PSA | Res-1 | Res-2 | 1,2-pentanediol | 1,2-propanediol | 1,2-decanediol | Glyceryl monocaprylate | GMIS-2 | Log Red. |
|---|---|---|---|---|---|---|---|---|---|
| HLB |  |  |  | 11.7 | 16.0 | 7.0 | 8.4 | 5.1 |  |
| CE-2 | 55 | — | — | 43 | — | — | — | — | 0.4 |
| CE-3 | 50 | 24 | — | — | 24 | — | — | — | 0.3 |
| B1 | 55 | — | 20.5 | — | — | 11.25 | 11.25 | — | 5.7 |
| B2 | 55 | — | — | — | — | 11.25 | 11.25 | 20.5 | 6.1 |
| B3 | 60 | — | — | — | — | 10 | 10 | 18 | 6.2 |

Both pentanediol (CE-2) and propanediol (CE-3) are hydrophilic vehicles (HLB>10) that effectively solubilize the CHG but do not plasticize the hydrophobic isooctyl acrylate rich domains of the adhesive. The antimicrobial activity of these compositions is very poor. In contrast, the use of hydrophobic vehicles such as 1,2-decanediol, glyceryl monocaprylate, and glyceryl isostearate (HLB<10) provided both good solubility of CHG and good compatibility with the hydrophobic domains resulting in very high log reductions.

Data Set C. These examples demonstrate the importance of using at least one vehicle capable of dissolving CHG as a plasticizer in the adhesive system in order to obtain surface activity. The formulations were prepared by premixing the vehicle or vehicle blends with aqueous CHG, diluting with heptane, and mixing the solution with a solvent based adhesive. The mixtures was coated on a silicone release liner at 4.6 mg/square centimeter, dried and laminated to Film 1. The adhesives were tested for antimicrobial activity using the Direct Time Kill Analysis with an incubation period of 15 minutes.

TABLE 7

Sample compositions (wt. %) prepared with PSA 3, and log reductions.

| Ex. | PSA | Decaglycerol pentaoleate (HLB = 7.2) | Glyceryl monocaprylate (HLB = 8.4) | 1,2-Decanediol (HLB = 7.0) | Ethylhexyl glycerin (HLB = 8.9) | CHG | Log Red. |
|---|---|---|---|---|---|---|---|
| CE-1 | 50 | 30 | 10 | 10 | — | 0 | 0 |
| A1 | 50 | 28 | 20 | — | — | 2 | 3.5 |
| A2 | 50 | 28 | 10 | 10 | — | 2 | 3.3 |
| A3 | 50 | 28 | — | — | 20 | 2 | 3.6 |

TABLE 9

Compositions (wt. %) and log reduction.

| EX. | PSA 3 | Sorbitan trioleate | GMIS-1 | GMIS-2 | Sorbitan isostearate | MCM | CHG | Log Reduction |
|---|---|---|---|---|---|---|---|---|
| CE-4 | 55 | — | — | 22.5 | 22.5 | — | 0 | 0.8 |
| CE-5 | 55 | 21.5 | 21.5 | — | — | — | 2 | 0.6 |
| CE-6 | 55 | — | 43 | — | — | — | 2 | 1.2 |
| C1 | 55 | — | — | 21.5 | 21.5 | — | 2 | 5.5 |
| C2 | 55 | — | — | — | 21.5 | 21.5 | 2 | 5.5 |
| C3 | 65 | — | — | — | — | 33 | 2 | 5.5 |

Dissolution experiments using lyophilized CHG showed that while GMIS-2 was a good solvent for CHG, the solubility of CHG in GMIS-1 and sorbitan trioleate was limited. Analytical tests showed that GMIS-2 contained a higher weight fraction of monoesterified compounds than GMIS-1, which is believed to contribute to the improvement in CHG solubility. Accordingly, the two adhesive samples containing GMIS-1 (CE-6) or GMIS and sorbitan trioleate (CE-5) showed very little efficacy with results comparable to CE-4, which did not contain CHG. The three remaining formulations, each of which used a hydrophobic vehicle(s) that solubilized CHG, showed almost complete bacterial kill.

Once incorporated into a resin system, compositions comprising CHG solubilized in a hydrophobic vehicle may be suitable for a wide variety of applications. For example, such compositions can be incorporated into a wide variety of articles including medical articles. Exemplary medical articles include drapes (e.g., surgical drapes and incise drapes), and dressings (e.g., wound dressings and I.V. dressings).

On exemplary article is illustrated in the FIGURE. Article 100 includes substrate 110 and CHG-containing composition 120 adhered to at least a portion of at least one surface of the substrate. In some embodiments, it is desirable to have a replenishable supply of CHG available at composition surface 125 to provide the desired persistent antimicrobial affect.

Generally, any known substrate may be used including, e.g., films, nonwovens, wovens, and combinations thereof. Substrates can be prepared from a wide variety of materials including, e.g., at least one of polyalkylenes, polyesters, polyamides, and polyurethanes. In some embodiments, composition 120 is directly bonded to substrate 110, as shown in the FIGURE. In some embodiments, the composition may be indirectly bonded to the substrate through one or more intermediate layers, including e.g., tie layers used to promote adhesion. The following examples illustrate exemplary embodiments of articles of the present disclosure.

Data Set D. These examples showed the effect of vehicle loading on surface availability and antimicrobial activity. The formulations were prepared by premixing MCM-1 with aqueous CHG, diluting with heptane, and mixing the solution with a solvent-based adhesive (PSA-1). MCM-1 is a hydrophobic vehicle that plasticized the hydrophobic phase of the PSA-1 adhesive. The mixture was coated on a silicone release liner at 4.6 mg/square centimeter, dried and laminated to Film-1. Surface extraction of the finished adhesive was performed according to the CHG Surface Availability Analysis to quantify the CHG released in quiescent water after 30 minutes. As the plasticizer fraction in the adhesive increased, there was a concomitant increase in the amount of CHG released per unit time. The effect of the difference in release can also be seen in the direct time kill data. The compositions, surface availability ("SA") reported as micrograms per square centimeter, and direct kill time results are summarized in Table 10.

TABLE 10

Compositions (wt. %), SA (micrograms/square centimeter) and log reductions.

| | | | | | Log Reduction | | | |
|---|---|---|---|---|---|---|---|---|
| EX. | PSA 1 | MCM-1 | CHG | SA | 5 min. | 10 min. | 15 min. | 20 min. |
| D1 | 75 | 23 | 2 | 4.2 | 4.4 | 5.3 | 5.7 | 5.7 |
| D2 | 50 | 48 | 2 | 7.5 | 5.5 | 5.7 | 5.7 | 5.7 |

Drape Adhesion Analysis. Pigskin was used as a proxy for human skin to gauge the adhesive performance of the adhesive article samples. The test method described in Grove, G. L. et al.; The Journal of Bone & Joint Surgery; Vol. 94A, No. 13; 2012; pp. 1187-1192, "Comparison of two preoperative skin antiseptic preparations and resultant surgical incise drape adhesion to skin in healthy volunteers" was followed with the following exceptions. Briefly, freshly euthanized pigs were clipped and shaved prior to prepping the skin with isopropyl alcohol. Each prepped area was allowed to dry for about 5 minutes and not more than 6 minutes. Strips cut 1.3 cm by 7.6 cm (0.5 in by 3 in) were applied in duplicate over the prepped area so that the long axis of the drape strip was orientated perpendicular to the pig's spine. To assure even application of the drape samples to the skin, a 2 kg (4.5 lb) roller was rolled over the drape samples once back and forth, using no additional pressure, immediately after the drape samples have been placed onto the test site. After the drape samples had been pressed in place with the roller, they were allowed to build adhesion for up to 5 minutes+/−30 seconds before any saline challenges were applied.

A 10 cm by 10 cm (4 in by 4 in) gauze that had been soaked in a 0.9% saline solution was placed over the drape sample immediately after the specified adhesion build time. Extra saline was added to the gauze at 10 minutes+/−2 minutes intervals during the challenge period to keep it saturated. The gauze was removed after 30 minutes+/−30 seconds. Immediately after removing the gauze from each sample, the drape sample was mechanically removed using a peel tester. The pull rate was 30.5 cm per minute (12 inches/min) at an angle of approximately 90 degrees to the skin. Data acquisition software was used to record the peel adhesion force.

Data Set E. These examples demonstrate the ability of adhesive articles prepared from adhesives plasticized with a hydrophobic vehicle containing CHG to adhere well to euthanized pigs under simulated irrigation. The control sample used was an antimicrobial incise drape marketed under the brand name IOBAN from 3M Company, St. Paul, Minn. Three CHG-containing, solvent-based adhesive formulations were prepared by combining 25 parts by weight PSA-3 (provided as 100 parts by weight of a solution containing 25 wt. % PSA-3 dissolved in ethyl acetate/methanol) with 25 parts by weight hydrophobic vehicle(s), 5 parts by weight of a 20 wt. % aqueous solution of CHG, and 75 parts by weight ethanol. Each adhesive was coated onto a silicone liner at 4.6 mg/square centimeter, dried, and laminated to Film-1 to prepare adhesive articles. The resulting compositions of the dried adhesives are summarized in Table 11. The results of the adhesion to pigskin under wet challenge are also summarized in Table 11. The reported values are the average and standard deviations are based on six replicates.

TABLE 11

Compositions (wt. %) and adhesion results in grams per 1.2 cm.

| | | | Vehicles | | | | Adhesion | |
|---|---|---|---|---|---|---|---|---|
| Ex. | PSA-3 | Res-2 | V1 | V2 | V3 | CHG | Average | Std. Dev. |
| E1 | 49 | — | 29.4 | 9.8 | 9.8 | 2 | 120 | 30 |
| E2 | 49 | 29.5 | — | 9.8 | 9.8 | 2 | 110 | 20 |
| E3 | 54 | — | 29.4 | 9.8 | 9.8 | 2 | 70 | 30 |
| CE-7 | Ioban (TV1) drape (3M Co.) | | | | | | 110 | 20 |

V1 = decaglycerol pentaoleate (HLB = 7.2)
V2 = glyceryl monocaprylate (HLB = 8.4)
V3 = 1,2-decanediol (HLB = 7.0)

In some embodiments, the ability to sterilize the final CHG-containing adhesive article, with, e.g., ethylene oxide (EO) or gamma irradiation, is a highly desired performance characteristic. For example, in some embodiments, it may be desirable to include the adhesive article in kits and be sterilized by EO as a part of those kits. The effect of EO sterilization on the adhesive formulation of Example E1 was evaluated. The sample was subject to a standard EO cycle and tested for antimicrobial activity using the Direct Time Kill Analysis at 5 minute and 30 minute incubation periods. No bacteria were detected after enumeration at both time periods, indicating complete kill. The sterilization cycle has no deleterious effect on the CHG activity in adhesive article.

It is known that aqueous CHG is unstable to gamma irradiation. In order to assess the effects of gamma radiation of CHG dissolved in non-aqueous solvents, two samples were prepared with a composition of 65% w/w PSA-3, 33% w/w MCM-1 and 2% w/w CHG. Example F1 was prepared without water with the CHG source being a 20% w/w solution of lyophilized CHG predissolved in MCM-1. In Example F2, the CHG source was a 20% w/w solution in water, with the water removed during drying. The samples were exposed to two different doses of gamma radiation: 25 and 45 kGy. These irradiated samples were then tested using the Direct Time Kill Analysis after 5 minutes of incubation. The results are shown in Table 12. Surprisingly, there was no negative effect of gamma irradiation observed on the CHG solubilized in non-aqueous vehicles. Furthermore, the activities were the same whether the CHG was pre-dissolved in the vehicle or dissolved in situ through the evaporation of water.

TABLE 12

Log reduction as a function of gamma radiation.

| | Gamma Dose | | |
|---|---|---|---|
| Ex. | None | 20 kGy | 45 kGy |
| F1 | 5.7 | 5.5 | 5.7 |
| F2 | 5.7 | 5.7 | 5.7 |

The effect of accelerated aging on the activity of CHG in the adhesive of an adhesive article was evaluated. Adhesive articles were prepared containing 58% w/w PSA-2, 20% w/w triacetin, 20% w/w glyceryl monocaprylate, and 2% w/w CHG. These samples were aged at 66° C. (150° F.) for six weeks. This aggressive aging schedule corresponds to two years aging at room temperature using the Van't Hoff rule. The samples were removed from the aging oven at the end of six weeks and tested for antimicrobial activity using the Direct Time Kill Analysis after 5 and 30 minutes of incubation. The aged samples showed a 0.2 log reduction after 5 minutes and a 3.1 log reduction after 30 minutes of incubation. Thus, there was considerable antimicrobial activity even after this extreme thermal treatment.

Data Set H. In some embodiments, a high Moisture Vapor Transmission Rate (MVTR) value may be desired, e.g., it may be desirable for CHG incise drape materials to prevent accumulation of moisture and skin maceration under the incise drape when it is applied for very long surgeries. Both the permeability properties of the backing and the adhesive (type and coat weight) impact MVTR.

To evaluate the MVTR of various drape examples, the following stock formulations were prepared. Formulation HA contained 49 wt. % PSA 2, 22.5% glycerol monoisostearate (GMIS-2), 22.5% sorbitan isostearate, 5% glycerol, and 1% CHG. Formulation HB was identical except ethylhexyl glycerin was used instead of the sorbitan isostearate. Drape examples H1-H4 were prepared by laminating formulations HA or HB to a HYTREL film backing. Tie layers were used in Examples H2-H4 to aide in bonding the formulations to the HYTREL backing.

Moisture Vapor Transmission Rate (MVTR) Analysis. The MVTR was determined using a variation of ASTM method E96-80. The film was placed adhesive side down over the opening of a standard glass vessel half filled with deionized water. The MVTR was determined by first allowing the sample 24 hours to equilibrate to the test conditions of 39 degree C. and 20% ambient relative humidity and then measuring the weight loss of water occurring over the following 24 hours.

TABLE 13

Compositions and moisture vapor transmission rates (g/sq meter/24 hours).

| EX. | Drape Composition Description | | MVTR | Std Dev |
|---|---|---|---|---|
| CE-8 | HYTREL film only | | 1380 | 17 |
| CE-9 | IOBAN Surgical Drape | | 470 | 13 |
| | Formulation | Tie-layer | | |
| H1 | HA (4.6 mg/cm$^2$) | None | 680 | 13 |
| H2 | HA (2.5 mg/cm$^2$) | PSA 2 (2.5 mg/cm$^2$) | 410 | 13 |
| H3 | HB (3.8 mg/cm$^2$) | PSA 4 (1.26 mg/cm$^2$) | 290 | 7 |
| H4 | HB (2.5 mg/cm$^2$) | PSA 4 (2.5 mg/cm$^2$) | 140 | 10 |

Data Set J. The primary function of an incise drape is to adhere well to the skin, providing a physical barrier that prevents the transfer of resident skin microorganisms into the surgical wound. This performance requirement is challenging for a skin-friendly adhesive to meet. After the adhesive film is applied to the patient, an incision is made with a scalpel. The deeper layers of tissue are then cut away using a combination of surgical instruments to gain access to the area of interest.

Adhesive performance of an incise drape must be evaluated using a combination of methods to assure adequate performance in the operating room. The drape must remain adhered to the skin all the way up to the edge throughout all of the manipulation performed in a typical surgery. In a typical surgery, a surgeon and nurse might insert and remove their hands, surgical instruments, implants, bones, and tissue multiple times over the course of several hours. The adhesive drape is also exposed to large volumes of irrigation fluid, saline, blood, and other bodily fluids, and must maintain its adhesion. After holding up to the challenges of a surgical procedure, the adhesive drape must still be relatively easy to remove from the skin, not causing significant pain or skin damage near the incision.

Peel testing on human or porcine skin is one accepted way to assess the performance of an adhesive tape or film on skin. Briefly, strips of adhesive coated backing are applied to the subject, allowed to adhere for a set dwell time, and removed using a device that measures the average force of removal at 90 degrees. The higher the force of removal (or peel value), the more difficult the adhesive is to remove from the skin surface. The peel value can give an indication of the ability of the adhesive construction to remain adhered to the skin. For an incise drape, a desirable peel value is the maximum value that does not cause significant pain or damage to the skin upon removal.

Based on historical product performance of 3M SteriDrape™ and Ioban™ products, typical dry peel testing does not accurately predict performance characteristics of an incise drape. To better mimic real surgical conditions, peel testing is performed after a relatively lengthy exposure to wet conditions. This type of testing has been found to predict more accurately the performance of incise drapes during surgery.

CHG-containing adhesives were prepared using a variety of base PSAs and vehicles. The adhesive formulations are summarized in Tables 14a, 14b, and 14c. All the active formulation layers were coated at 4.6 mg/square centimeter.

TABLE 14a

Compositions (wt. %) for formulations prepared with PSA-1.

| EX. | PSA 1 | Res-4 | Res-4 | GMO* | GMIS-2 | Glycerol | CHG |
|---|---|---|---|---|---|---|---|
| J1 | 74 | 10.7 | — | 10.7 | — | 3.6 | 1 |
| J2 | 64 | — | 15 | — | 15 | 5 | 1 |
| J3 | 64 | — | 15 | 15 | — | 5 | 1 |

*GMO = glycerol monooleate

TABLE 14b

Compositions (wt. %) for formulations prepared with PSA-2.

| EX. | PSA 2 | Res-2 | 1,2-pentanediol | Glycerol | CHG |
|---|---|---|---|---|---|
| J4 | 64 | 15 | 15 | 5 | 1 |

TABLE 14c

Compositions (wt. %) for formulations prepared with PSA-3.

| EX. | PSA 3 | Res-3 | Res-4 | GMO* | 1,2-pentanediol | Glycerol | MCM-2 | CHG |
|---|---|---|---|---|---|---|---|---|
| J5 | 59 | 20 | — | 20 | — | — | — | 1 |
| J6 | 54 | 22.5 | — | 22.5 | — | — | — | 1 |
| J7 | 59 | — | 20 | 20 | — | — | — | 1 |
| J8 | 64 | — | 15 | — | 15 | 5 | — | 1 |
| J9 | 59 | — | 20 | 20 | — | — | — | 1 |
| J10 | 54 | — | 22.5 | 22.5 | — | — | — | 1 |
| J11 | 64 | — | 15 | — | — | 5 | 15 | 1 |

*GMO = glycerol monooleate

Incise drape samples prepared using these adhesives and tested for adhesion performance by peel testing under wet conditions on the side skin of a freshly euthanized pig. After the animal was euthanized, hair was removed by shaving with a razor using only water. 70% IPA was then used to clean the skin surface, and allowed to dry for 10 minutes. Drape samples cut into 1.3 cm by 7.6 cm (0.5 inch by 3 inch) strips were then applied to the prepared skin such that the long axis of the drape sample was oriented perpendicular to the spine. The drapes were then allowed to build adhesion for up to 5 minutes. After the dwell time, 10 cm by 10 cm (4 inch by 4 inch) gauze pieces soaked in 0.9% saline solution were placed over the drape samples. Extra saline was added to the gauze at ten minutes intervals during the challenge period to keep it saturated for up to thirty minutes. After thirty minutes, the wet gauze was removed and samples were removed at a 90 degree angle, mechanically with a peel tester. The force of removal for each strip was recorded using four replicates. The results were compared to a commercially available products; Ioban™ 2 Antimicrobial Incise Drape ("Drape 1") available from 3M Company, St. Paul, Minn. The averages and standard deviations are reported in Table 15.

These samples were also tested to further determine potential performance in real applications. For the Mock Surgery test, freshly excised porcine belly skin with underlying tissue intact (thickness ranging from 1.3 to 3.8 cm) (0.5 inch to 1.5 inch) was stretched taught across a board with nails. Hair was removed by dry clipping with an electric razor (#50 blade). The skin was then cleaned with 70% IPA and allowed to dry for 15 minutes. Approximately 7.6 by 12.7 cm (3 inch by 5 inch) drape samples were then applied to the skin, smoothed with gauze, and allowed to dwell and build adhesion for five minutes. After the dwell time, a new #10 scalpel blade was used to make a shallow 6 cm incision through the first few layers of skin using a single stroke of the blade. Then the blade was used to cut through the remaining tissue using several strokes, but without further disturbing the initial cut. After the incision was made, gloved hands were used to pull and stretch the incision in a semi-aggressive manner, ensuring that the drape/skin interface was contacted and rubbed by the gloves. This was continued for two minutes.

After two minutes, the incision edges were examined for areas where the adhesive drape had lifted away from the skin. Drape 1 remained adhered to the incision edge around the entire wound. Repeat testing of this product using this method has shown that this drape reliably does not lift from the wound edge for more than 1 cm of the total incision edge (12 cm for a 6 cm incision). Therefore, the performance of this commercial drape under mock surgical conditions was used as the acceptance criteria for experimental drape performance. These results are also shown in Table 15.

TABLE 15

Peel Adhesion and Mock Surgery test results for Example Set J.

| EX. | Average Peel Force (g) n = 4 | Standard Deviation | Mock Surgery Wound Manipulation Test |
|---|---|---|---|
| Drape 1 | 90 | 44 | Pass |
| J1 | 108 | 25 | Pass |
| J2 | 165 | 64 | Pass |
| J3 | 143 | 29 | Fail |
| J4 | 38 | 2 | Fail |
| J5 | 72 | 25 | Pass |
| J6 | 97 | 14 | Pass |
| J7 | 134 | 39 | Pass |
| J8 | 44 | 10 | Fail |
| J9 | 119 | 35 | Fail |
| J10 | 102 | 15 | Fail |
| J11 | 39 | 11 | Fail |

The results show that several of the experimental drape samples had average peel values greater than or equivalent to the Ioban™ incise drape product. Based on the peel force data, one would expect that these drapes might perform equivalently to or better than such commercial incise drapes. The data also show observations from more rigorous performance testing of the incise drape samples under conditions mimicking surgery. In this test, some of the experimental drapes having a high peel value and did not perform well under simulated surgical conditions; thus, peel force alone cannot be used to predict adhesive performance of experimental incise drape constructions.

Data Set K. In some embodiments, the static dissipative properties of an adhesive article may be important for safe and proper handling and application. When the liner is removed from an adhesive, buildup of static may occur. Such static can cause blocking to occur, and can make the drape film attract to itself, making the product very difficult to apply. In some embodiments, the final construction might be required to meet the specifications for minimizing the risk of spark generation per NFPA 99. The specifications require that the article pass a static decay test where 5 kV of charge is dissipated in less than 0.5 seconds.

Static Dissipation Analysis. In some embodiments, the adhesive article must meet the specifications for minimizing the risk of spark generation per NFPA 99. The specifications require that the article pass a static decay test where 5 kV of charge is dissipated in less than 0.5 seconds (per industrial test method: IST 40.2-92 "Electrostatic Decay").

Generally, adhesives by themselves are very hydrophobic and are not static dissipative. Usually an anti-static coating is put on the backing or liner to meet these specifications. In some embodiments, the adhesive formulations can be prepared with vehicles that impart static dissipative properties. The adhesive formulations described in Table 16a coated at 4.6 mg/square centimeter on Film-1 were tested for static dissipation. The static dissipation results are shown in Table 16b. Formulations K1, K2, and K3 easily met the NFPA static dissipation requirements.

TABLE 16a

Compositions (wt. %) for Data Set K.

| EX. | PSA-1 | PSA-2 | Res-2 | GMIS-2 | Glycerol | MCM-1 | Sorbitan isostearate | CHG |
|---|---|---|---|---|---|---|---|---|
| K1 | 63 | — | 15 | 15 | 5 | — | — | 2 |
| K2 | 64.5 | — | 15 | 15 | 5 | — | — | 0.5 |
| K3 | — | 50 | — | 16 | — | 16 | 16 | 2 |
| K4 | — | 50 | — | 24 | — | — | 24 | 2 |
| K5 | — | 50 | — | 49 | — | — | — | 1 |

TABLE 16b

Static dissipation results.

| EX. | Static decay time (sec.) | |
| --- | --- | --- |
|  | (+) | (−) |
| K1 | 0.34 | 0.32 |
| K2 | 0.30 | 0.32 |
| K3 | 0.07 | 0.07 |
| K4 | 0.83 | 0.79 |
| K5 | 1.24 | 1.18 |

Data Set L. Ex vivo samples were conducted using the compositions summarized in Table 17. The standard sampling solution ("SSS") was 75 mM phosphate-buffered water (0.04% $KH_2PO_4$, 1.01% $Na_2HPO_4$) containing 0.1% TRITON X-100 with 3% Polysorbate 80, 0.3% lecithin and 0.1% sodium thiosulfate at pH 7.9±0.1. Various procedures were used to evaluate performance with the results summarized in Tables 18a, 18b, and c.

TABLE 17

Compositions (% w/w) for Data Set L.

| Ex. | Description | PSA 1 | Res-2 | GMIS-2 | Glycerol | CHG |
| --- | --- | --- | --- | --- | --- | --- |
| L1 | Placebo | 65 | 15 | 15 | 5 | 0 |
| L2 | Active | 63 | 15 | 15 | 5 | 2 |

Procedure I: Analysis of drapes on porcine skin seeded with *Serratia marcescens*. This experiment evaluated the effects of the active and placebo drapes on the intact skin under the drapes after both were in place for 4 hours. Recovery of the seeded bacteria from both the skin and drape were combined to determine the total antimicrobial effect.

1. Cut porcine abdominal skin into two sections and stretch out on board. Remove hair by clipping and wipe away gross contamination.
2. Prepare a $10^8$ CFU/mL suspension of *Serratia marcescens* in Phosphate-Buffered Water (PBW) from an overnight growth plate. Dilute 1:10 in PBW for $10^7$ CFU/mL working suspension. This is used to inoculate the skin.
3. Saturate the sponge of a DURAPREP 8635 applicator (available from 3M Co.) with the *Serratia* working suspension. Start in the middle of the area and wipe the sponge over the skin back and forth, moving out from center in both directions. Re-saturate the same sponge and repeat with fresh suspension, changing direction by 90 degrees. Next use same sponge but do not re-saturate. Wipe from center out in a third direction. Let skin dry completely (30 minutes).
4. Mark three areas in center of area to be draped by marking bottom of a scrub ring with a sterile skin marker and touching to the skin. Remove liners from drape pieces and apply to skin. Smooth over top with sterile gauze. Mark areas on drape to correspond with the marked areas on the skin.
5. Collect two baseline samples from inoculated areas around the drapes by the cup scrub method (ASTM E1874-09).
6. Leave drapes in place for four hours at 35° C.
7. After four hours on skin, remove each drape and place on a clean liner. Scrub marked areas of skin underneath the drape using the cup scrub method (ASTM E1874-09). Serially dilute collected solutions; spread plate neat and diluted solutions on Trypticase Soy Agar (TSA) plates.
8. Die cut three 25 mm samples from the marked areas on each drape. Transfer each separately to 20 mL Neutralizing Buffer (Difco) containing 0.1% sodium thiosulfate. Sonicate for one minute and vortex vigorously for two minutes. Serially dilute and spread plate all neat and diluted solutions on TSA plates.
9. Incubate plates at 32° C. for three days.
10. Count red colonies only (*Serratia*) on plates. Calculate bacteria recovered per square centimeter. Add bacteria from correlating skin and drape sites, and convert to log 10. Calculate the average of the triplicate sites per drape.

TABLE 18a

Log Recovery (n = 3) for drapes on seeded porcine skin (*Serratia marcescens*).

| EX. | Average Log Recovery | Standard deviation |
| --- | --- | --- |
| L1 | 4.1 | 0.2 |
| L2 | 3.4 | 0.4 |

Procedure II: Incision Model on Seeded Porcine Skin (*Serratia marcescens*). This model evaluates the active and placebo drapes in a simulated surgical procedure with shallow incisions through skin, retraction and manipulation. The use of seeded bacteria localizes the bacteria of interest to the skin surface initially and can be differentiated from normal flora.

1. Stretch and nail porcine abdominal skin to board. Clip hair and wipe away gross contamination.
2. Prepare a $10^8$ CFU/mL suspension of *Serratia marcescens* in Phosphate-Buffered Water (PBW) from an overnight growth plate. Dilute 1:10 in PBW for $10^7$ CFU/mL working suspension. This is used to inoculate the skin.
3. Saturate the sponge of a DURAPREP 8635 applicator with the *Serratia* working suspension. Start in the middle of the area and wipe the sponge over the skin back and forth, moving out from center in both directions. Re-saturate the same sponge and repeat with fresh suspension, changing direction by 90 degrees. Next use same sponge but do not re-saturate. Wipe from center out in a third direction. Let skin dry completely (30 minutes).
4. Collect baselines samples of bacteria. Place sterile metal template onto skin (in area NOT covered by drapes). Prewet sterile swab in 1 ml SSS and rub swab on skin within template for 30 seconds. Return swab to 1 ml tube, vortex 30 seconds, serially dilute and plate in TSA.
5. Apply drape to skin, using sterile gauze to smoothly place drape and adhere it to the skin.
6. Allow each drape to sit for five minutes.
7. With a sterile scalpel blade (no. 10), make a six centimeter incision through the drape. Cut through the fatty layer and into the muscle, but not completely through the piece of skin to avoid contamination from the underside of the skin section (approximately 1-2 cm deep).
8. With sterile gloved fingers, manipulate the incision for one minute. Use the first two fingers on each hand to move around inside the incision and pull at the wound edges.
9. Check for lifting of the drape along the incision edge.
10. Retract incision approximately three centimeters with sterile stainless steel 5.5" Weitlaner retractor.
11. Moisten sterile gauze (two pieces of 12 ply gauze) with 25 ml sterile phosphate-buffered water (PBW) and place loosely over the retracted incision.

12. Repeat process for a total of three incisions on each drape section.

13. Cover skin with foil pan (loose) and incubate at 35° C. for a total of four hours.

14. After one hour, remove skin from incubator and remove gauze and retractors. Manipulate incision edges for fifteen seconds by rubbing with gloved fingers around the incisions (on top of drape). Replace retractors (keep retractors matched to their original incisions) and cover with new moistened gauze. Cover with foil pan and return to 35° C. incubator.

15. Repeat step 14 after two total hours and again after three total hours.

16. After four hours, remove gauze and retractors. Evaluate each incision for drape lift and visible fluid under the drapes.

17. Collect bacteria along the edges of each incision. Prewet a sterile swab in a 1 ml tube of SSS and roll the swab twice around the inside of the incision. Break off swab into the tube of SSS and vortex for thirty seconds. ("In incision" sample).

18. Peel drape off of skin. Look for moisture on skin that may have migrated under the drape.

19. Collect bacteria from skin around incision edge. Prewet a sterile swab in a 1 ml tube of SSS and roll the swab once around the edge of the incision on the skin surface. Break off the swab into the tube of SSS and vortex for thirty seconds. ("Surrounding skin" sample).

20. Serially dilute solutions with swabs and spread plate each onto Trypticase Soy Agar (TSA) plates.

21. Incubate plates for three days at 32° C.

22. Calculate bacteria per mL (swab). Calculate the mean of the incisions per drape. Convert to log 10 CFU/swab.

TABLE 18b

| | Log Recovery (n = 9) Incision Model on Seeded Porcine Skin (*Serratia marcescens*). | | | |
|---|---|---|---|---|
| | "In incision" results | | "Surrounding skin" results | |
| EX. | Average Log Recovery | Standard deviation | Average Log Recovery | Standard deviation |
| L1 | 3.0 | 0.3 | 4.4 | 0.2 |
| L2 | 2.2 | 0.4 | 3.7 | 0.2 |

There are differences between the placebo and active drapes with respect to the incision edges and on the skin immediately surrounding the incision. In both instances, there is lower log recovery from the active drape (L2) than from the placebo drape (L1). The active drape is superior to the placebo drape in the incision (95% confidence).

Procedure III: Incision Model on Porcine Skin (Normal Flora). This model evaluates the active and placebo drapes in a simulated surgical procedure with shallow incisions through skin, retraction and manipulation. Procedure III was identical to Procedure II, except that Steps 2 and 3 were not performed. Also, a modified Standard Sampling Solution was prepared with Tamol ("SST") containing 75 mM phosphate-buffered water (0.04% $KH_2PO_4$, 1.01% $Na_2HPO_4$) containing 0.1% TRITON X-100 with 1% Polysorbate 80, 0.3% lecithin and 1% Tamol with pH 7.9±0.1 was used.

TABLE 18c

| | Log Recovery (n = 6) Incision Model on Porcine Skin (Normal Flora). | | | |
|---|---|---|---|---|
| | "In incision" | | "Surrounding skin" | |
| EX. | Average Log Recovery | Standard deviation | Average Log Recovery | Standard deviation |
| L1 | 2.4 | 0.5 | 4.0 | 0.8 |
| L2 | 1.3 | 0.4 | 3.0 | 0.5 |

There are differences between the placebo and active drapes with respect to the incision edges and on the skin immediately surrounding the incision. The 1 log difference in the incision is statistically significant with a p-value of <0.001. There is a 1 log difference on the skin surface also, however it was not statistically significant (p-value of 0.17).

Various modifications and alterations of this invention will become apparent to those skilled in the art without departing from the scope and spirit of this invention.

What is claimed is:

1. A composition comprising chlorhexidine gluconate solubilized in a hydrophobic vehicle having a hydrophilic-lipophilic balance of no greater than 10 as determined using the HLB Method,
    wherein the hydrophobic vehicle comprises two proximate hydrogen-bonding groups,
    wherein at least one of the hydrogen-bonding groups is a hydrogen donor,
    wherein the composition comprises no greater than 2 parts by weight hydrophilic vehicle per 1 part by weight chlorhexidine gluconate, and
    wherein the hydrophobic vehicle is a monoacylglycerol.

2. The composition of claim 1, wherein an alkyl group of the monoacylglycerol is a C8 to C18 alkyl group.

3. The composition of claim 1, wherein the alkyl group of the monoacylglycerol is a C8 to C18 alkyl group.

4. The composition of claim 1, wherein the monoacylglycerol is selected from the group consisting of glycerol monocaprylate, glycerol monolaurate, glycerol monoisostearate, glycerol monooleate, and combinations thereof.

5. The composition of claim 1, wherein the monoacylglycerol is selected from the group consisting of glycerol monocaprylate, glycerol monoisostearate, glycerol monooleate, and combinations thereof.

6. The composition of claim 1, wherein the composition comprises no greater than 1 part by weight water per 1 part by weight chlorhexidine gluconate.

7. The composition of claim 6, wherein the composition comprises no greater than 0.1 parts by weight water per 1 part by weight chlorhexidine gluconate.

8. The composition of claim 1, wherein the monoacylglycerol is a 1-monoacylglyceride.

9. The composition of claim 1, wherein the composition comprises no greater than 1 part by weight hydrophilic vehicle per 1 part by weight chlorhexidine gluconate.

10. The composition according to claim 1, further comprising a resin system comprising a polymer.

11. The composition of claim 10, wherein the resin system comprises a hydrophobic phase, wherein the hydrophobic vehicle plasticizes the hydrophobic phase.

12. The composition of claim 10, wherein the polymer comprises an acrylate polymer.

13. The composition of claim 10, wherein the polymer comprises a block copolymer polymer.

14. The composition according to claim 10, wherein the resin system is a pressure sensitive adhesive.

15. An article comprising a substrate and the composition according to claim 1 bonded to at least a portion of a surface of the substrate.

16. The article according to claim 15, wherein the article is a medical article.

17. A mixture comprising:
- a composition comprising chlorhexidine gluconate solubilized in a hydrophobic vehicle, wherein the hydrophobic vehicle is a monoacylglycerol;
- a resin system comprising a hydrophobic phase, wherein the hydrophobic vehicle plasticizes the hydrophobic phase,
- wherein the hydrophobic vehicle and the solubilized chlorhexidine gluconate are capable of migrating to a surface of a layer of the resin system providing a replenishable supply of chlorhexidine gluconate to the surface.

18. The mixture of claim 17, wherein the resin system comprises an alkyl (meth)acrylate monomer, wherein the alkyl group has 4 to 18 carbon atoms.

19. The mixture of claim 17, wherein the composition comprises no greater than 2 parts by weight hydrophilic vehicle per 1 part by weight chlorhexidine gluconate.

20. The mixture of claim 19, wherein the composition comprises no greater than 1 part by weight water per 1 part by weight chlorhexidine gluconate.

* * * * *

UNITED STATES PATENT AND TRADEMARK OFFICE
CERTIFICATE OF CORRECTION

PATENT NO. : 10,456,509 B2
APPLICATION NO. : 16/262981
DATED : October 29, 2019
INVENTOR(S) : Vinod Menon et al.

It is certified that error appears in the above-identified patent and that said Letters Patent is hereby corrected as shown below:

On the Title Page

Page 2, item (56), In the References Cited under "Other Publications":
Column 2, Line 7, delete "www,ijsr.net." and insert -- www.ijsr.net. --
Column 2, Line 27, delete "Equillbration" and insert -- Equilibration --

In the Specification

Column 13-14, Line 25, delete "Bl" and insert -- B1 --

Column 17, Line 29, delete "(TV1)" and insert -- (TM) --

Signed and Sealed this
Thirtieth Day of June, 2020

Andrei Iancu
*Director of the United States Patent and Trademark Office*